United States Patent [19]

Gibson

[11] Patent Number: 4,871,839
[45] Date of Patent: Oct. 3, 1989

[54] SKIN TREATMENT COMPOSITION

[75] Inventor: Walter T. Gibson, Northamptonshire, England

[73] Assignee: Lever Brothers Company, New York, N.Y.

[21] Appl. No.: 22,193

[22] Filed: Mar. 5, 1987

[30] Foreign Application Priority Data

Mar. 14, 1986 [GB] United Kingdom ............... 8606368

[51] Int. Cl.$^4$ .................. A61K 7/48; A61K 7/06; A61K 31/70; A61K 31/72
[52] U.S. Cl. ................................ 536/55.1; 514/880
[58] Field of Search .............. 514/880, 230.8, 235.8, 514/275; 536/55.1

[56] References Cited

U.S. PATENT DOCUMENTS 4,139,619  2/1979  Chidsey, III ............... 514/230.8
4,761,401  8/1988  Couchman et al. ............ 536/4.1

FOREIGN PATENT DOCUMENTS

85/04577  10/1985  PCT Int'l Appl. .
86100616  1/1986   PCT Int'l Appl. .

OTHER PUBLICATIONS

"Journal of Pharmaceutical Sciences", 64, (1975), pp. 1366–1371.

Primary Examiner—Ronald W. Griffin
Attorney, Agent, or Firm—Milton L. Honig

[57] ABSTRACT

A composition suitable for topical application to human skin, particularly the scalp comprises a minoxidil glucuronide together with a cosmetically and/or physiologically acceptable vehicle. The composition is particularly suited to stimulating hair growth or regrowth.

11 Claims, No Drawings

SKIN TREATMENT COMPOSITION

FIELD OF THE INVENTION

The invention relates to cosmetic and pharmaceutical compositions for topical application to human skin, containing a derivative of minoxidil which is particularly useful in promoting or enhancing the growth of hair, especially on the human scalp.

BACKGROUND

The Hair Growth Cycle

It should be explained that in most mammals, hair does not grow continuously, but undergoes a cycle of activity involving alternate periods of growth and rest. The hair growth cycle can be divided into three main stages, namely:
 (i) the growth phase known as anagen, during which the hair follicle penetrates deep into the dermis with the cells of the bulb dividing rapidly and differentiating to form the hair,
 (ii) the transitional stage known as catagen which is heralded by the cessation of mitosis, and during which the follicle regresses upwards through the dermis and hair growth ceases,
 (iii) the resting stage known as telogen in which the regressed follicle contains a small secondary germ with an underlying ball of tightly packed dermal papilla cells.

The initiation of a new anagen phase is revealed by rapid cell proliferation in the germ, expansion of the dermal papilla and elaboration of basement membrane components. The hair cycle is then repeated many times until, as a consequence of the onset of male pattern baldness, most of the hair follicles spend an increasing proportion of their time in the telogen stage, and the hairs produced become finer, shorter and less visible; this is known as terminal to vellus transformation.

PRIOR ART

Hair growth

Although there have been many claims in the scientific literature to the promotion or maintenance of hair growth, by the topical application of hair tonics and the like, none has ever been proven to be sufficiently free from disadvantageous clinical side effects when administered topically, orally or systemically to warrant commercial exploitation as a proprietary medicine or as a cosmetic product. Perhaps the only means which has met with partial success for growing hair on the bald or balding human head is by transplantation of hair to the bald areas. This is however an extremely painful operation and is not always successful. Furthermore, it is immediately apparent to the casual observer that the subject has received a hair transplant, and it may take many months or even years before the hair regrowth, following this operation, assumes an appearance which resembles that of the original naturally growing hair.

Among the many hair regrowth studies that have been reported in the literature, the work of Bazzano as described in PCT International Publication No. WO 85/04577 is worthy of mention. This publication describes a composition useful for increasing the rate of hair growth on mammalian skin, prolonging the anagen phase of the hair growth cycle and for treating various types of alopecias, the composition comprising an effective amount of a compound chosen from:

methyl-5-[3,6-dihydro-1(2H)-pyridyl]-2-oxo-2H-[1,2,4]-oxadiazolo[2,3-a] pyrimidine-7-carbamate, having the structure:

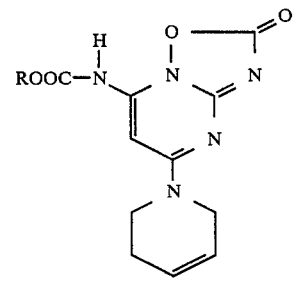

where R is methyl; or analogues thereof where R is ethyl, butyl, iso-butyl, benzyl or 2-methoxyethyl;

methyl-2-amino-6-[3,6-dihydro-1(2H)-pyridyl]-4-pyrimidine carbamate-3-oxide, having the structure:

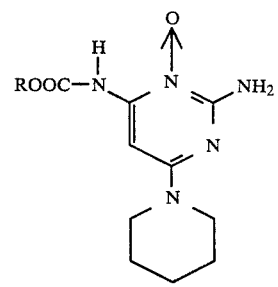

where R is methyl; or analogues thereof where R is ethyl, butyl, iso-butyl, benzyl or 2-methoxyethyl; methyl-5-[3,6-dihydro-1(2H)-pyridyl]-2-oxo-2H-[1,2,4]-oxadiazolo[2,3-1] pyrimidine-7-carbamate, having the structure:

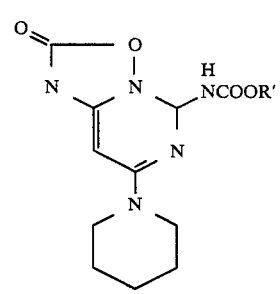

where R' is methyl; or analogues thereof where R' is ethyl, butyl, iso-butyl, methoxyethyl or allyl; and dimethyl-6-[3,6-dihydro-1(2H)-pyridyl] 2,4-pyrimidine dicarbamate-3-oxide, having the structure:

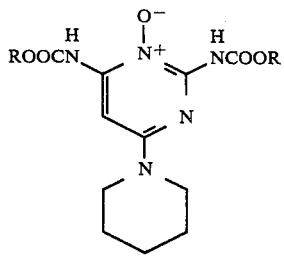

(4)

where R is methyl; or analogues thereof where R is ethyl, butyl, iso-butyl, benzyl or 2-methoxyethyl.

It has also been reported in U.S. Pat. No. 4,139,619 to Chidsey assigned to the Upjohn Company that a topical composition comprising:
6-amino-1,2-dihydro-1-hydroxy-2-imino-4-piperidinopyrimidine, also known as 6-(1-piperidinyl)-2,4-pyrimidinediamine 3-oxide, or minoxidil
having the structure:

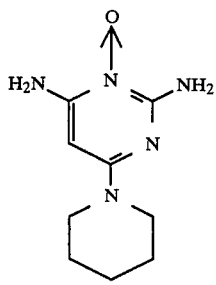

(5)

as the free base or acid addition salts thereof, or certain specified related iminopyrimidines, is useful in stimulating the conversion of vellus hair to growth as terminal hair, as well as increasing the rate of growth of terminal hair.

Minoxidil is a potent antihypertensive drug which has a number of side effects including hypertrichosis following systemic application, as reported by Burton J L & Marshall A., in 1979 in "Hypertrichosis due to minoxidil", published in the British Journal of Dermatology 70, 593–595.

In spite of the apparent stimulation of hair growth or regrowth reported independently by Bazzano and by Chidsey, following topical application of minoxidil or related compounds, there is still general concern that systemic side-effects can result, particularly following topical application of minoxidil itself, see for example:
Yates V M, King C M & Harrap B (1984) "Topical minoxidil in the treatment of *alopecia areata*". Br. Med. J.288 1087.
Ranchoff R E & Bergfeld W F (1985) "Topical minoxidil reduces blood pressure," J.American Academy of Dermatology, 12 586–587.
Novak E, Franz T J, Headington J T & Wester R C, "Topically applied minoxidil in baldness" (1985) Int J Dermatol 24 82–87.
Franz T J, (1985) "Percutaneous absorption of minoxidil in man". Arch Dermatol, 121 203–206.

These reports highlight the potential for percutaneous adsorption of minoxidil leading to systemic side effects. Moreover, it is also generally recognized in the medical literature that the side effects of orally administered minoxidil are very serious, and include fluid retention, tachycardia, dyspnoea, gynaecomastia, fatigue, nausea and cardiotoxicity. It would accordingly be advantageous to employ a form of minoxidil which had been detoxified before topical application to avoid the possibility of such side effects, while still retaining the ability to promote hair growth.

It has been reported in the scientific press, notably by:
Gottlieb T B, Thomas R L & Chidsey C A (1972) "Pharmacokinetic studies of minoxidil", Clin. Pharmacol. Ther., 13, 436–441; and
Thomas R L & Harpootlian H (1975) "Metabolism of minoxidil, a new hypotensive agent. II Biotransformation following oral administration to rats, dogs and monkeys." J. Pharm. Sci., 64, 1366–1371,
that the principle circulating metabolite of minoxidil in the human subject is the glucuronide, and that this metabolite is excreted in the urine following oral administration of minoxidil. Because glucuronidation acts as a signal for excretion, it would be expected that the glucuronide conjugate of minoxidil would be less toxic than minoxidil itself, since it would be more rapidly cleared from the body. Glucuronidation in most cases also leads to pharmacological inactivation of drugs, and for this reason also, minoxidil glucuronide should be a safer but far less efficacious compound. Accordingly, it would be logical to expect that the ability of such a molecule to enhance hair growth or to promote regrowth would be lost as a consequence of detoxification.

We have now discovered that preformed minoxidil glucuronide, when applied topically to the skin surprisingly stimulates hair growth or regrowth, promoting the transition of vellus hairs to terminal hairs.

DEFINITION OF THE INVENTION

The invention accordingly provides a composition suitable for topical application to human skin, particularly to the scalp, which composition comprises a minoxidil glucuronide, together with a cosmetically and/or physiologically acceptable vehicle.

DISCLOSURE OF THE INVENTION

The Minoxidil Glucuronide

The composition according to the invention comprises a minoxidil glucuronide, this being a conjugate of minoxidil and glucuronic acid. It is believed that various conjugates of minoxidil and glucuronic acid can be formed by biotransformation, notably minoxidil-O-glucuronides, but possibleyalso minoxidil-N-glucuronides, and that these molecules, or mixtures of them, can promote hair growth or regrowth when applied topically to human skin.

Minoxidil-O-glucuronide can occur in at least two forms represented by structures (6) and (7) as follows:

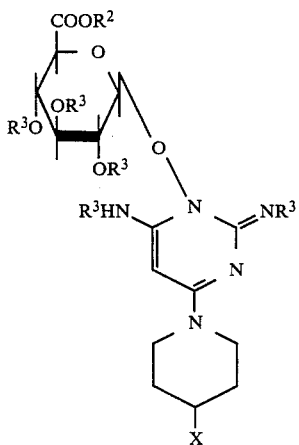

(6)

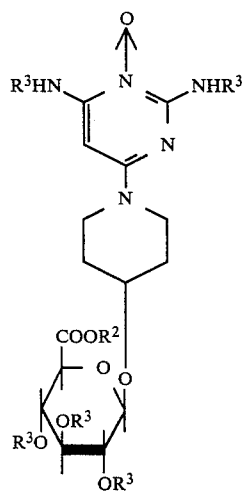

(7)

Minoxidil-N-glucuronide can occur in at least in two forms represented are the structures (8) and (9) as follows:

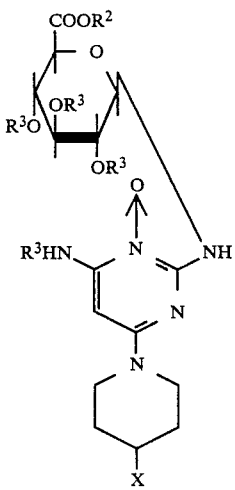

(8)

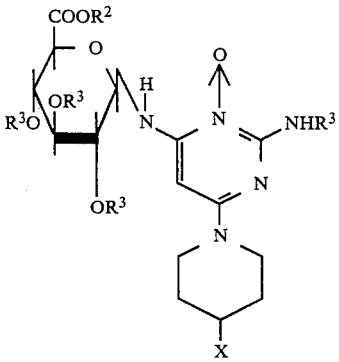

(9)

where
X is - H or —OH;
$R^2$ is - H or $C_1$ to $C_{10}$ alkyl
$R^3$ is - H, $C_1$ to $C_4$ alkyl, $C_2$ to $C_4$ acyl or $SO_3M$; and
M is - H, or a metallic or organic cation.

The amount of the minoxidil glucuronide to be incorporated with a suitable vehicle into compositions for topical use can vary widely, but in general, an amount of from 0.001 to 20%, preferably from 0.01 to 10% and ideally from 0.02 to 5% by weight of the composition will provide an adequate dose to the skin after topical application.

The Vehicle

The composition according to the invention also comprises a solid, semi-solid or liquid cosmetically and/or physiologically acceptable vehicle, to enable the minoxidil glucuronide to be conveyed to the skin at an appropriate dilution. The nature of the vehicle will depend upon the method chosen for topical administration of the composition. The vehicle can itself be inert or it can possess physiological or pharmaceutical benefits of its own.

The selection of a vehicle for this purpose presents a wide range of possibilities depending on the required product form of the composition. Suitable vehicles can be classified as described hereinafter.

It should be explained that vehicles are substances which can act as diluents, dispersants, or solvents for the minoxidil glucuronide and which therefore ensure that it can be applied to and distributed evenly over the hair and/or scalp at an appropriate concentration. The vehicle is preferably one which can aid penetration of the minoxidil glucuoronide into the skin to reach the immediate environment of the hair follicle. Compositions according to this invention can include water as a vehicle, and/or at least one cosmetically acceptable vehicle other than water.

Vehicles other than water that can be used in compositions according to the invention can include solids or liquids such as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polyethylene glycol, triethylene glycol, lanolin, caster oil, acetylated lanolin alcohols, petroleum, mineral oil, butyl myristate, isostearic acid, palmitic acid, isopropyl linoleate, lauryl lactate, myristyl lactate, decyl oleate, myristyl, myristate;

Propellants, such as trichlorofluoromethane, dichlorodifluoromethane, dichlorotetrafluorethane, monochlorodifluoromethane, trichlorotrifluorethane, propane, butane, isobutane, dimethyl ether, carbon dioxide, nitrous oxide;

Solvents, such as ethyl alcohol, methylene chloride, isopropanol, castor oil, ethylene glycol monoethyl ether, diethylene glycol monobutyl ether, diethylene glycol monoethyl ether, dimethyl sulphoxide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The amount of vehicle in the composition, including water if present, should preferably be sufficient to carry at least a portion of the minoxidil glucuronide to the skin in an amount which is sufficient effectively to enhance hair growth. The amount of the vehicle can comprise from 10 to 99.999% by weight of the composition, or the balance of the composition, that is from 80 to 99.999% by weight, when no other ingredients are present. When the composition contains other optional ingredients, such as those hereinafter described, then the vehicle can accordingly comprise from 10 to 99.5%, preferably from 50 to 99% by weight of the composition.

Perfume

The composition according to the invention can also optionally comprise a perfume in an amount sufficient to make the composition acceptable to the consumer and pleasant to use. Usually, the perfume will form from 0.01 to 10% by weight of the composition.

Activity Enhancer

The composition according to the invention can also optionally comprise an activity enhancer whose presence further improves the delivery to the skin of the minoxidil glucuronide. The activity enhancer accordingly effectively increases the partition of the minoxidil glucuronide into the skin from the composition when applied topically.

While screening a series of non-electrolytes for their ability to function as activity enhancers, it was observed that they were all compounds which were capable of substantially increasing the cloud point temperature of nonionic surfactants. Such compounds included short chain alkanols, diols and short chain fatty acids. By contrast, other non-electrolytes which reduce the cloud point temperature of nonionic surfactants, such as long chain alcohols, for example, butan-1-ol and cyclohexanol; polyols, for example sorbitol and propan-1,2,3-triol, do not function as activity enhancers.

An activity enhancer is accordingly defined as a non-electrolyte which is capable, at a concentration of 5% by weight of increasing the cloud point temperature of a 0.025M aqueous solution of polyoxyethylene(8)nonylphenyl ether by at least 10° C. Preferably the activity enhancer is one which is capable of increasing the cloud point temperature by at least 15° C., most preferably by at least 20° C.

It should be explained that the "cloud point" is a measure of the inverse solubility of a nonionic surfactant with temperature and can be determined by heating a standard clear aqueous solution of the nonionic surfactant until the solution becomes visibly cloudy and then measuring the temperature.

The cloud point temperature can conveniently be determined automatically using the equipment and method described by Baum et al in Mat. Res. Std. 4 26 (1964).

Examples of suitable compounds functioning as activity enhancers, together with the respective elevated cloud point temperature obtained in each case when using the standard test defined hereinbefore are listed below in Table 1.

TABLE 1

Elevation of the cloud point temperature of a 0.025 M aqueous solution of polyoxyethylene(8)nonylphenyl ether in the presence of activity enhancers

| Activity Enhancer (5% by weight) | 0.025 M aqueous solution of polyoxyethylene(8)nonyl phenyl ether (SYNPERONIC NP8 ex ICI) | |
|---|---|---|
| | Cloud point temperature (°C.) | Elevation of cloud point temperature |
| None (control) | 33.5 | 0 |
| 2-methyl propan-2-ol | 55.0 | 21.5 |
| Propan-2-ol | 56.0 | 22.5 |
| Ethyl-2hydroxypropanoate | 52.1 | 18.6 |
| Hexan-2,5-diol | 52.0 | 18.5 |
| POE(2) ethyl ether | 46.0 | 12.5 |
| Di(2-hydroxypropyl) ether | 44.8 | 11.3 |
| Pentan-2,4-diol | 48.0 | 14.5 |
| Acetone | 46.3 | 12.8 |
| POE(2) methyl ether | 43.5 | 10.0 |
| 2-hydroxypropionic acid | 45.0 | 11.5 |
| Propan-1-ol | 53.0 | 19.5 |
| 1,4 Dioxane | 44.0 | 10.5 |
| Tetrahydrofuran | 45.0 | 11.5 |
| Butan-1,4-diol | 45.0 | 11.5 |

By way of comparison, we list below in Table 2 example of non-electrolytes which do not satisfy the cloud point test in that the increase in cloud point temperature is less than 10° C.; in some cases a reduction of cloud point temperature is observed.

TABLE 2

Elevation (or reduction) of the cloud point temperature of a 0.025 M aqueous solution of polyoxyethylene(8)nonylphenyl ether in the presence of compounds which are not "activity enhancers" as herein defined

| Compound which is not an activity enhancer (5% by weight) | 0.025 M aqueous solution of polyoxyethylene(8)nonylphenyl phenyl ether (SYNPERONIC NP8) | |
|---|---|---|
| | Cloud point temperature (°C.) | Elevation of cloud point temperature (°C.) |
| None (control) | 33.5 | 0 |
| 2-methyl propan-1-ol | 41.0 | 7.5 |
| Butan-1-ol | 36.3 | 2.8 |
| Cyclohexanol | 11.0 | −22.5 |
| Ethan-1,2-diol | 33.0 | −0.5 |
| Propan-1,2-diol | 39.0 | 5.5 |

TABLE 2-continued

Elevation (or reduction) of the cloud point temperature of a 0.025 M aqueous solution of polyoxyethylene(8)nonylphenyl ether in the presence of compounds which are not "activity enhancers" as herein defined

| Compound which is not an activity enhancer (5% by weight) | 0.025 M aqueous solution of polyoxyethylene(8)nonylphenyl phenyl ether (SYNPERONIC NP8) | |
|---|---|---|
| | Cloud point temperature (°C.) | Elevation of cloud point temperature (°C.) |
| Butan-1,3-diol | 41.5 | 8.0 |
| Propan-1,2,3-triol | 32.2 | −1.3 |
| Morpholine | 40.0 | 6.5 |
| Dimethyl sulphoxide | 33.9 | 0.4 |

The activity enhancer should form from 0.1 to 50%, preferably from 0.5 to 25% by weight of the product.

It should be explained that compounds which do not behave as activity enhancers as defined herein can nonetheless be included in compositions according to the invention as vehicles.

Other ingredients

The composition according to the invention can contain ingredients other than those already mentioned, depending on the form of the intended product. It is, for example, possible to include antiseptics, preservatives, antioxidants, emulsifiers, colouring agents and detergents.

The composition according to the invention can also be employed as a vehicle for a wide variety of cosmetically or pharmaceutically active ingredients, particularly ingredients which have some beneficial effect when applied to the skin other than the promotion of hair growth.

Process

The invention also provides a process for the preparation of a composition suitable for topical application to the hair and/or scalp which comprises mixing a minoxidil glucuoronide with a suitable vehicle to provide a concentration of from 0.01 to 10% by weight.

Product Form

The compositions of the invention can be formulated as liquids, for example as a lotion, shampoo, milk or cream for use in conjunction with an applicator such as a roll-ball applicator, or a spray device such as an aerosol can containing propellant, or a container fitted with a pump to dispense the liquid product. Alternatively, the compositions of the invention can be solid or semi-solid, for example sticks, creams or gels, for use in conjunction with a suitable applicator or simply a tube, bottle or lidded jar, or as a liquid-impregnated fabric, such as a tissue wipe.

The invention accordingly also provides a closed container containing a composition as herein defined.

The invention also provides for the use of a minoxidil glucuronide in the topical treatment of baldness.

Use of compositions

The compositions according to the invention are primarily intended for topical application to the scalp of the human subject, particularly where the head is already bald or balding. The compositions can also be applied profilactically to the hair and hence the scalp to reduce or prevent the onset of baldness.

The invention accordingly also provides a method for the conversion of vellus hair to growth as terminal hair, which comprises applying to mammalian skin in the region of vellus hair, an effective amount of the composition. Furthermore, the invention also provides a method for increasing the rate of terminal hair growth in mammalian species, which comprises applying to mammalian skin in the region of terminal hair, an effective amount of the composition.

The "effective amount" of the composition and the frequency of its application to the hair and/or scalp can vary widely, depending on personal needs, but it is suggested by way of example that topical application of from 1 to 5 g daily of a composition containing from 0.001 to 10 g of a selected minoxidil glucuronide over the period of at least six months will in most cases result in an improvement in hair growth.

EXAMPLES

The invention is illustrated by the following examples:

Example 1

This Example illustrates a lotion according to the invention which is suitable for topical application to the scalp in order to promote hair growth.

The lotion has the following formulation:

| | % w/w |
|---|---|
| minoxidil glucuronide: structure (6) | 0.1 |
| ethanol | 99.995 |
| perfume | q.s |

Example 2

This Example illustrates a hair tonic which is suitable for application to hair or scalp.

The hair tonic has the following formulation:

| | % w/w |
|---|---|
| minoxidil glucoronide: structure (7) | 0.8 |
| ethanol | 50 |
| water | 49 |
| perfume | q.s. |

Example 3

This Example also illustrates a lotion which is suitable for topical application to the scalp.

The lotion has the following formulation:

| | % w/w |
|---|---|
| minoxidil glucuronide: structure (8) | 1.5 |
| propan-2-ol | 10 |
| ethanol | 88.5 |
| perfume | q.s. |

Example 4

This Example also illustrates a hair tonic which is suitable for application to hair or scalp.

The hair tonic has the following formulation:

| | % w/w |
|---|---|
| minoxidil glucuronide: structure (9) | 0.2 |

|  | % w/w |
|---|---|
| ethanol | 40 |
| water | 59.80 |
| perfume | q.s. |

Examples 5 to 8

The following formulations represent lotions which can be used topically in the treatment of bald or balding male or female heads.

|  | % w/w | | | |
|---|---|---|---|---|
|  | 5 | 6 | 7 | 8 |
| Hydroxyethyl cellulose | 0.4 | — | 0.4 | — |
| Absolute ethanol | 25 | 25 | 25 | 25 |
| Propane-1,2-diol | — | — | 38.4 | 38.4 |
| Butane-1,3-diol | 38.4 | 38.8 | — | — |
| Paramethyl benzoate | 0.2 | 0.2 | 0.2 | 0.2 |
| Minoxidil glucuronide: structure (6) | 5 | — | — | — |
| Minoxidil glucuronide: structure (7) | — | 1 | — | — |
| Minoxidil glucuronide: structure (8) | — | — | 0.8 | — |
| Minoxidil glucuronide: structure (9) | — | — | — | 0.6 |
| Perfume | 1 | 1 | 1 | 1 |
| Water to | 100 | 100 | 100 | 100 |

Example 9 to 12

The following formulations represent creams which can be used in the treatment of baldness.

|  | % w/w | | | |
|---|---|---|---|---|
|  | 9 | 10 | 11 | 12 |
| Cetyl alcohol polyoxyethylene (10) | 4 | 4 | 4 | 4 |
| Cetyl alcohol | 4 | 4 | 4 | 4 |
| Mineral oil | 4 | 2 | — | — |
| Paraffin wax | — | 2 | 4 | — |
| Partial glyceride of palmitic and stearic acids | — | — | — | 4 |
| Minoxidil glucuronide: structure (6) | 2 | — | — | — |
| Minoxidil glucuronide: structure (7) | — | — | — | 1 |
| Minoxidil glucuronide: structure (8) | — | 1.5 | — | — |
| Minoxidil glucuronide: structure (9) | — | — | 2 | — |
| Triethanolamine | 0.75 | 0.75 | 0.75 | 0.75 |
| Butane-1,3-diol | 3 | 3 | 3 | 3 |
| Xanthan gum | 0.3 | 0.3 | 0.3 | 0.3 |
| Preservative | 0.4 | 0.4 | 0.4 | 0.4 |
| Perfume | q.s. | q.s. | q.s. | q.s. |
| Water to | 100 | 100 | 100 | 100 |

Example 13

This Example illustrates a water-in-oil high internal phase emulsion containing a novel disaccharide according to the invention.

The emulsion consisted of 10% by volume oily phase and 90% by weight aqueous phase.

The oily phase and the aqueous phase had the following constitution:

|  | % w/w |
|---|---|
| Oily phase | |
| Sorbitan monooleate | 20 |
| Quarternium-18 hectorite | 5 |
| Liquid paraffin | 75 |
| Aqueous phase | |
| Minoxidil glucuronide: (6) | 0.5 |
| Xanthan gum | 1 |
| Preservative | 0.3 |
| Perfume | q.s. |
| Sodium chloride (1% w/w solution) to | 100 |

The emulsion was prepared by taking 10 parts by volume of the oily phase and to it adding slowly with stirring 90 parts by volume of the aqueous phase.

The high internal phase water-in-oil emulsion so formed can be applied topically to the scalp, to improve hair growth and regrowth.

The following examples 14 to 18 illustrate shampoos for use in washing the hair and scalp, and for promoting hair growth on the scalp.

Example 14

|  | % w/w |
|---|---|
| Sodium lauryl ether sulphate (2 EO): 21% AD | 41.4 |
| Lauryl dimethylamino acetic acid betaine* 30% AD | 4 |
| Coconut fatty acid diethanolamine | 1.5 |
| Oleyl triethoxy phosphate (BRIPHOS O3D) | 1 |
| Polyglycol-polyamine condensation resin (POLYQUART H): 50% active | 1.5 |
| Preservative, colouring matter, salt | 0.58 |
| Minoxidil glucuronide: structure (6) | 5 |
| Perfume | q.s. |
| Water to | 100 |

Example 15

|  | % w/w |
|---|---|
| Sodium lauryl ether sulphate (2 EO): 100% AD | 12 |
| POLYQUART H: 50% active | 2.5 |
| BRIPHOS O3D | 2.5 |
| Minoxidil glucuronide: structure (7) | 4 |
| Perfume | q.s. |
| Water to | 100 |

Example 16

|  | % w/w |
|---|---|
| Monoethanolamine lauryl sulphate: 100% AD | 20 |
| POLYQUART H: 50% active | 3 |
| BRIPHOS O3D | 1.7 |
| Coconut diethanolamide | 5 |
| Minoxidil glucuronide: structure (8) | 1 |
| Perfume | q.s. |
| Water to | 100 |
| pH adjusted to 6.5 | |

Example 17

|  | % w/w |
|---|---|
| Sodium lauryl ether sulphate (3 EO): | 12 |

-continued

| | % w/w |
|---|---|
| 100% AD | |
| POLYQUART H: 50% active | 0.3 |
| BRIPHOS O3D | 1 |
| Minoxidil glucuronide: structure (9) | 2 |
| Perfume | q.s. |
| Water to | 100 |
| pH adjusted to 6.5 | |

Example 18

| | % w/w |
|---|---|
| Sodium lauryl ether sulphate (2 EO): 100% AD | 12 |
| POLYQUART H: 50% active | 3 |
| BRIPHOS O3D | 1 |
| Opacifier | 9 |
| Minoxidil glucuronide: structure (6) | 5 |
| Perfume | q.s. |
| Water to | 100 |
| pH adjusted to 6.5 | |

Examples 19 to 24

The following Examples 19 to 24 illustrate powder compositions according to the invention which can be applied topically to the scalp.

| | % w/w | | | | | |
|---|---|---|---|---|---|---|
| | 19 | 20 | 21 | 22 | 23 | 24 |
| Chemically modified starch | 5 | — | 5 | — | 5 | — |
| Chemically modified cellulose | — | 5 | — | 5 | — | 5 |
| Boric acid | 10 | 10 | 10 | 10 | 10 | 10 |
| Zinc oxide | 5 | 5 | 5 | 5 | 5 | 5 |
| Minoxidil glucuronide: structure (6) | 5 | — | — | — | 3 | — |
| Minoxidil glucuronide: structure (7) | — | 10 | — | — | 2 | — |
| Minoxidil glucuronide: structure (8) | — | — | 2 | — | — | 2 |
| Minoxidil glucuronide: structure (9) | — | — | — | 4 | — | 5 |
| Perfume | q.s. | q.s. | q.s. | q.s. | q.s. | q.s. |
| Chalk | 10 | 10 | 10 | 10 | 10 | 10 |
| Talc to | 100 | 100 | 100 | 100 | 100 | 100 |

We claim:
1. A composition suitable for topical application to human skin, which comprises:
   (i) from 0.001 to 20% by weight of a minoxidil glucuronide, and
   (ii) from 10 to 99.999% by weight of a cosmetically and/or physiologically acceptable vehicle.
2. The composition of claim 1, wherein the minoxidil glucuronide is a minoxidil-O-glucuronide having the structure:

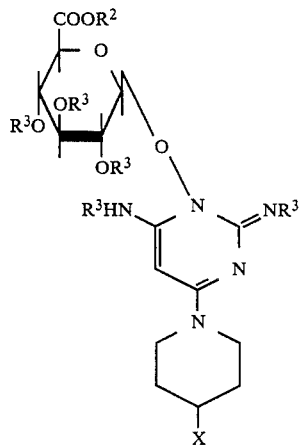

(6)

where

X is - H or —OH;

$R^2$ is - H or $C_1$ to $C_{10}$ alkyl $R^3$ is - H, $C_1$ to $C_4$ alkyl, $C_2$ to $C_4$ acyl or $SO_3M$; and M is - H, or a metallic or organic cation.

3. The composition of claim 1, wherein the minoxidil glucuronide is a minoxidil-O-glucuronide having the structure:

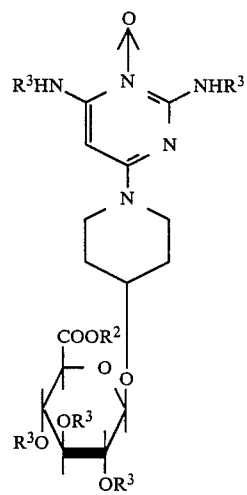

(7)

where $R^2$ is - H or $C_1$ to $C_{10}$ alkyl $R^3$ is - H, $C_1$ to $C_4$ alkyl, $C_2$ to $C_4$ acyl or $SO_3M$; and M is - H, or a metallic or organic cation.

4. The composition of claim 1, wherein the minoxidil glucuronide is a minoxidil-N-glucuronide having the structure:

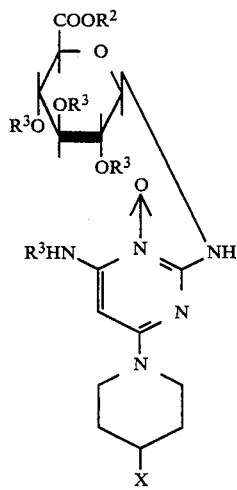
(8)

where

X is - H or —OH;

$R^2$ is - H or $C_1$ to $C_{10}$ alkyl $R^3$ is - H, $C_1$ to $C_4$ alkyl, $C_2$ to $C_4$ acyl or $SO_3M$; and M is - H, or a metallic or organic cation.

5. The composition of claim 1, wherein the minoxidil glucuronide is a minoxidil-N-glucuronide having the structure:

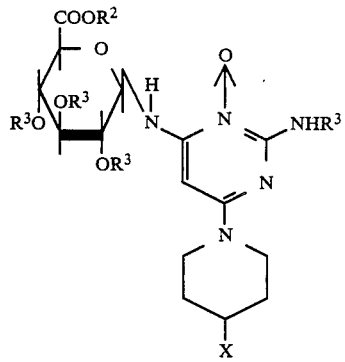
(9)

where

X is - H or —OH;

$R^2$ is - H or $C_1$ to $C_{10}$ alkyl $R^3$ is - H, $C_1$ to $C_4$ alkyl, $C_2$ to $C_4$ acyl or $SO_3M$; and M is - H, or a metallic or organic cation.

6. The composition of claim 1, wherein the minoxidil glucuronide forms from 0.01 to 10% by weight of the composition.

7. The composition of claim 1, wherein the minoxidil glucuronide forms from 0.02 to 5% by weight of the composition.

8. The composition of claim 1, wherein the vehicle forms from 10 to 99.5% by weight.

9. The composition of claim 1 which additionally comprises a perfume.

10. The composition of claim 1, which additionally comprises an activity enhancer.

11. The composition of claim 1, which is in the form of a cream, a gel, a lotion or a stick.

* * * * *